United States Patent
Katzir et al.

(10) Patent No.: US 6,864,498 B2
(45) Date of Patent: Mar. 8, 2005

(54) OPTICAL INSPECTION SYSTEM EMPLOYING A STARING ARRAY SCANNER

(75) Inventors: Yigal Katzir, Rishon Lezion (IL); Avraham Adler, Nof Ayalon (IL); Itay Gur-Arie, Rishon Lezion (IL)

(73) Assignee: Orbotech Ltd., Yavne (IL)

( * ) Notice: Subject to any disclaimer, the term of this patent is extended or adjusted under 35 U.S.C. 154(b) by 63 days.

(21) Appl. No.: 10/141,988

(22) Filed: May 10, 2002

(65) Prior Publication Data

US 2002/0166983 A1 Nov. 14, 2002

Related U.S. Application Data

(60) Provisional application No. 60/290,011, filed on May 11, 2001.

(51) Int. Cl.[7] .............................................. G01N 21/88
(52) U.S. Cl. ..................... 250/559.45; 250/234; 356/23
(58) Field of Search ....................... 250/559.45, 559.42, 250/559.04, 559.05, 559.06, 234; 356/23–26; 359/34, 39

(56) References Cited

U.S. PATENT DOCUMENTS

| | | | |
|---|---|---|---|
| 4,877,326 A | 10/1989 | Chadwick et al. | 356/394 |
| 5,085,517 A | 2/1992 | Chadwick et al. | 356/394 |
| 5,131,755 A | 7/1992 | Chadwick et al. | 356/394 |
| 5,172,005 A | 12/1992 | Cochran et al. | 250/57 |
| 5,365,084 A | 11/1994 | Cochran et al. | 250/571 |
| 5,750,985 A | 5/1998 | Suzuki | 250/234 |
| 5,909,302 A | 6/1999 | Guissin et al. | 359/225 |
| 6,061,086 A * | 5/2000 | Reimer et al. | 348/125 |
| 6,525,333 B1 * | 2/2003 | Hooker et al. | 250/559.45 |

FOREIGN PATENT DOCUMENTS

WO    WO 02/056084 A1    7/2002

OTHER PUBLICATIONS

Brochure: *SK–75™ AOI Inspection System, Advanced Inspection for Process Sampling and Volume Production*, Orbotech Ltd.
Product Information on SK–75™ AOI Inspection System, Orbotech Ltd., Orbotech Website: http:www.Orbotech.com/products_mi_sk75.html.
Brochure: *Inspire–9060™ Specifications*, Orbotech Ltd.
Product Information on Inspire–9000™ Automated Optical Inspection System, Orbotech Ltd., Orbotech Website: http:www.Orbotech.com/products_mi_inspire9000.html.

* cited by examiner

Primary Examiner—Thanh X. Luu
Assistant Examiner—Seung C. Sohn
(74) Attorney, Agent, or Firm—Sughrue Mion, PLLC (57) ABSTRACT

A scanner system acquires images of articles using a sensor acquiring an image of a portion of an article and defining a field of view, a displacer operative to provide mutual relative displacement between the article and the sensor at a generally uniform rate of displacement, and a field of view freezer operative to provide a generally motionless image during image acquisition. The scanner system is particularly useful in the field of automated optical inspection.

48 Claims, 5 Drawing Sheets

OPTICAL INSPECTION SYSTEM EMPLOYING A STARING ARRAY SCANNER

CROSS REFERENCE TO RELATED APPLICATION

This application claims the benefit of U.S. Provisional Application No. 60/290,011, filed May 11, 2001, which is incorporated by reference, herein, in its entirety.

FIELD OF THE INVENTION

The following invention relates to systems for the automated optical inspection of objects, and more particularly to systems for the automated optical inspection of electrical circuits.

BACKGROUND OF THE INVENTION

Electrical circuit inspection systems are well known, and include INSPIRE-9060™ and SK-75™ automated optical inspection systems commercially available from Orbotech Ltd. of Yavne, Israel. These systems employ an illuminator illuminating a portion of an electrical circuit to be inspected, a conveyor conveying the electrical circuit so that the illuminated portion progressively illuminates successive portions thereof, and a line CCD sensor viewing the illuminated portion and outputting an image of the electrical circuit. Considerable effort has been made to provide inspection system architectures that increase the intensity and quantity of light that is effectively available to image electrical circuits undergoing automated optical inspection, and/ or to improve the quality of images that may be acquired by scanner systems.

SUMMARY OF INVENTION

The present invention seeks to provide improved systems for the automated optical inspection of electrical circuits.

In accordance with a general aspect of the invention there is provided a system for scanning an object to obtain an image, wherein the system employs a two dimensional sensor acquiring a plurality of two-dimensional images of the object. Means are provided to scan the object while the object is in continuous translation relative to the sensor without substantially smearing the image. In accordance with an embodiment of the invention, a strobing light source is used in order to minimize image smearing. The duty cycle of the strobing light source preferably is in the range between 1:5 and 1:1000, however a strobing light having a duty cycle in excess of 1:1000 may be used, provided that it has a sufficient level of brightness.

In accordance with another general aspect of the invention, a scanning system including a two dimensional sensor is provided to acquire a plurality of two dimensional images of an object while the object is being displaced relative to the sensor. The images are provided to a defect analyzer to detect defects in the object. When taken together the images comprise substantially all parts of the object which it is desired to inspect. Pulsed illumination is employed to minimize, or eliminate, image smearing.

In accordance with another general aspect of the invention, an scanning image acquisition system employing a two dimensional sensor is provided. An opto-mechanical element is also provided to intermittently freeze a field of view of the sensor relative to the object, during scanning, while an image is being acquired by the sensor.

In accordance with another general aspect of the invention there is provided a scanning system for obtaining multiple, precisely aligned, images of an object, preferably with a single sensor. The system is particularly suited, for example, for obtaining a color image of an object in which each of the component red, green and blue images is acquired in temporal sequence, and is precisely, and essentially absolutely, aligned with each other. Optionally, corresponding images are each acquired with a different composition of light impinging on the object. For example in each corresponding image, illumination is provided to impinge on the object at different angle of illumination or illumination is provided with a different polarization. The different compositions of light are provided in temporal sequence.

In accordance with an embodiment of the invention a system for automated optical inspection includes a sensor that is arranged to acquire at least one image of an article to be inspected while the article and the sensor are mutually being translated relative to each other. The sensor is configured and arranged so that its field of view extends at least partly along an axis lying in a direction of mutual translation between the sensor and the article. An optical element is provided to translate a field of view viewed by the sensor in coordination with a relative translation between the sensor and the article such that the location of the field of view of the sensor is held substantially motionless relative to the article for a finite period of time during mutual the mutual translation of the sensor and the article.

Various embodiments of the invention include one or more of the features which follow.

The article is an electrical circuit, for example a printed circuit board, ball grid array substrate, multi-chip module, flat panel display or integrated circuit.

The sensor is a two-dimensional sensor array comprising sensor elements, or pixels, viewing a portion of the article, wherein the portion of the article viewed by the sensor elements extends in a first direction generally along an axis of translation between the sensor array and the article, and in a second direction generally crosswise to the axis of translation.

The mutual translation between the sensor and the article proceeds at a generally uniform rate over a portion of the object, and the sensor defines a field of view which is translated at a generally non-uniform rate over the portion of the object.

The mutual translation between the sensor and the article is generally continuous, and the optical element is arranged so that during the generally continuous mutual translation between the sensor and the article, the spatial orientation of the optical element relative to the sensor and/or relative to the article being inspected is changed from a first spatial orientation to a second spatial orientation. The spatial orientation of the optical element may be periodically reset from the second spatial orientation to the first spatial orientation, such that images of successive, partially overlapping 2-dimensional portions of the article may be acquired.

A charge on pixels forming the sensor array is accumulated during a change in the orientation of the optical element relative to the sensor from a first spatial orientation to a second spatial orientation. Accumulated charge on pixels is transferred from the sensor array, for example to a transfer register, while the orientation of the optical element is reset to the first spatial orientation.

The system includes an illuminator illuminating the portion of the article viewed by the sensor while the orientation of the optical element is changed from the first spatial orientation to the second spatial orientation. The illuminator is turned off while charge that has accumulated on pixels is transferred from the sensor.

The system includes one or more illuminators providing red, green and blue illumination respectively. While the orientation of the optical element is changed from the first spatial orientation to the second spatial orientation during translation of the sensor relative to the article, such that the location of the field of view of the sensor is held generally motionless relative to the article for a finite period of time, a first image is acquired while the article is illuminated with a first color of illumination and a second image is acquired while the article is illuminated with a second color of illumination. Optionally, a third image is acquired while the article is illuminated with a third color of illumination. The colors of illumination are, for example, red, green and blue. After an image with each of the different colors of illumination is acquired, the relative spatial orientation of the optical element relative to the sensor, or the article, is reset and the process is repeated.

The optical element is a planar mirror or a multi-faceted rotating polygon, a transparent rotating window, a transparent rotating polygon, or any other suitable passive or active optical element operative to affect a lateral translation of an image.

In other embodiments the sensor, instead of the object, is translated during image acquisition, thus obviating the need of a movable optical element.

BRIEF DESCRIPTION OF DRAWINGS

The present invention will be understood and appreciated more fully from the following detailed description, taken in conjunction with the drawings in which.

DETAILED DESCRIPTION OF PREFERRED EMBODIMENTS

Figure 1:
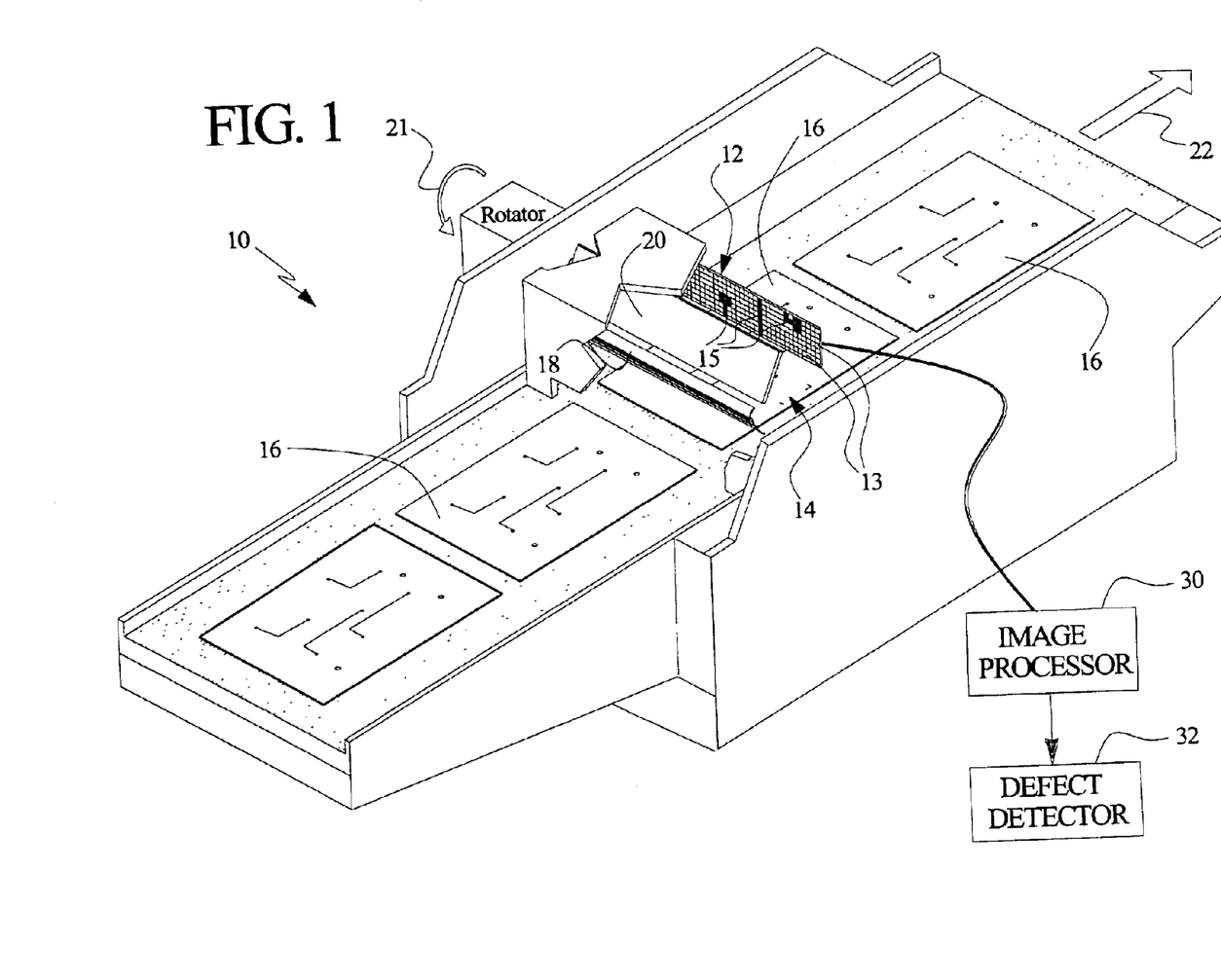
FIG. 1 is a simplified partially cut away pictorial illustration of an inspection system configured and operative in accordance with an embodiment of the invention.

Reference is made to FIG. 1 which is a simplified partially cut away pictorial illustration of an inspection system 10 configured and operative in accordance with an embodiment of the invention. System 10 is useful, for example, for inspecting flat articles such as electrical circuits. Although the following disclosure describes the present invention in the context of inspection of a system for inspecting electrical circuit substrates, the system and methods described herein may be useful for inspecting any suitable article of manufacture, and in particular electrical circuits. As used herein, the terms electrical circuits and electrical circuit substrates include, without limitation, printed circuit boards, ball grid array substrates, multi-chip modules and flat panel displays, as well as various generally planar layers that may be combined together to form a completed electrical circuit.

In accordance with an embodiment of the invention, system 10 includes an imaging sensor 12, which may be any suitable two dimensional imaging sensor, such as a CCD (Charge Coupled Device) type or CMOS (Complementary Metal Oxide Semiconductor) type sensor. Sensor 12 is defined by an array of pixels 13, and is arranged to view a portion 14 of an article to be inspected 16, such as an electrical circuit substrate used in the manufacture of printed circuit boards. Suitable optics (not shown) are provided in order to form an image 15 of portion 14 on sensor 12. In accordance with an embodiment of the invention, an illuminator 18 is operative to illuminate portion 14 during the acquisition of an image, or images, by sensor 12.

It is a feature of the present invention that system 10 acquires a plurality of two-dimensional images, each of which image is of a different portion of article 16. Another feature of the present invention is that system 10 includes means for briefly freezing an image impinging on sensor 12, such as an image of portion 14, while article 16 and sensor 12 are generally continuously mutually translated relative to each other. Thus as seen in FIG. 1, system 10 includes a movable optical element 20 disposed in an optical path extending between sensor 12 and portion 14. In FIG. 1, movable optical element 20 is depicted as a planar mirror that rotates in the direction of arrow 21 while articles 16 are displaced relative to sensor 12 in the direction of arrow 22. Any other suitable configuration of a movable optical element, such as a multi-faceted rotating polygon, a transparent rotating window, a transparent rotating polygon, or any other suitable passive or active optical element operative to affect a lateral translation of an image may be employed in system 10.

It is noted that an alternative way to freeze an image of portion 14 on sensor 12 is to provide sufficiently short flashes of illumination, for example using suitable short pulses of light from LED, xenon, laser or other suitable light sources.

In FIG. 1, sensor 12, illuminator 18, and optical element 20 are depicted as being attached to the chassis of system 10 at only one end. It is appreciated that FIG. 1 is merely a conceptual illustration of system 10. In actuality the configuration and design of system 10, including the mode of fastening of sensor 12, illuminator 18 and optical element 20 to the chassis of system 10, are likely to be different from what is shown.

In accordance with an embodiment of the invention, the rotation of the movable optical element 20 in the direction of arrow 21 is synchronized with displacement of an article 16 in the direction of arrow 22 such that while optical element is rotating in the direction of arrow 21, the field of view of sensor 12 is translated. As a result, when the mutual translation between an article 16 and sensor 12 are suitably synchronized with the changing spatial orientation of optical element 20, from a first spatial orientation to a second spatial orientation, the field of view of sensor 12 remains frozen over portion 14 for a brief, but finite, period of time.

In accordance with an embodiment of the invention, the change in spatial orientation of optical element 20 includes both pivot and linear motions in order to ensure that an image of portion 14 is maintained in focus at sensor 12 as element 20 is rotated. A preferred structure for imparting a suitable change in the spatial orientation of element 20 relative to sensor 12 is described in U.S. Pat. No. 5,909,302, the disclosure of which is incorporated herein by reference in its entirety.

After each brief, but finite, period of time during which the field of view of sensor 12 is frozen at a portion 14, the mutual orientation of article 16 and sensor 12 has changed. Once the change in mutual orientation between article 16 and sensor 12 approaches the limit of what can be accommodated by a change in the spatial orientation of optical element 20, the spatial orientation of optical element 20 is reset to its initial spatial orientation. As a result of such reset, the field of view of sensor is moved to a successive portion of article 16.

In accordance with an embodiment of the invention, the spatial orientation of optical element 20 is again changed, e.g. by rotation, in synchronicity with the mutual translation of article 16 and sensor 12 to freeze the field of view of sensor 12 over the successive portion of article 16. This process is repeated in progression to acquire a collection of images, which, when taken together, form an image of substantially the entirety of a surface of article 16.

In accordance with an embodiment of the invention, illuminator 18 includes a light source and a lens or a shaped reflector operative to direct from light to the illuminator to portion 14. The light source may be, for example, light emitting diode, xenon flash, pulsed laser (such as Q-switched laser), a halogen or metal halide light source in combination with a suitable shutter, or any other suitable light source, providing generally wide spectrum illumination (such as "white" light), or light within a desired spectral range or monochrome light (such as colored light). The illumination may be visible or non-visible light such as UV or IR radiation. In order to produce light within a desired spectral range, the illuminator may employ spectral filters or suitable light sources, such as light emitting diodes, operative to emit light in a desired spectral range. The lens, or shaped reflector, is preferably configured to produce illumination confined to portion 14 to minimize stray light.

In accordance with an embodiment of the invention, as seen in FIG. 1, system 10 is provided with a translator (not shown) operative to translate articles 16 in the direction indicated by arrow 22, in a direct throughput manner. This is not the only manner in which articles 16 can be translated. Optionally, the translator is operative to translate any combination of articles 16, or an assembly including sensor 12, illuminator 18 and optical element 20 along an axis indicated by arrow 22. The translator may be operative in a direct throughput mode, as seen in FIG. 1, in a serpentine mode, or in a raster mode in which each article 16 to be inspected is scanned in a plurality of swaths.

It is further seen in FIG. 1 that the images acquired with sensor 12 are provided to an image processor 30. Thus, images each of the successive portions 14 are processed by image processor 30 and provided to a defect detector 32 which is operative to analyze the images and to detect defects in articles 16, such as electrical circuits. It is appreciated that, as known in the art of electrical circuit inspection, images of the successive portions 14 may be compared to, or analyzed with reference to, any combination of various design rules, a reference image prepared from a CAD or CAM file (not shown), an image of another electrical circuit which is known to be not defective, images of other portions of article 16, or any other suitable image. Moreover, images of successive portions 14 may be each processed individually or combined into a larger image for processing.

In accordance with an embodiment of the invention, an output of defect detector 32 is employed, for example, in quality control. In electrical circuit manufacture, after a pattern of conductors is formed on an electrical circuit substrate, the substrate is inspected. An output of defect detector 32 may be relied upon to approve non-defective electrical circuit substrates, or to repair or reject defective electrical circuit substrates.

Reference is now made to FIGS. 2A–2E which are highly simplified schematic diagrams illustrating the operation of a system 110 useful for the automated optical inspection of electrical circuits in accordance with an embodiment of the invention. System 110 preferably includes a sensor 112, such as a CCD type sensor formed of a plurality of pixels 113, arranged to view a portion 114 of an object to be inspected 116 such as an electrical circuit substrate used in the manufacture of printed circuit boards. Suitable optics (not shown) are provided in order to form an image of portion 114 on sensor 112.

It is noted that although the present invention is described in a general context, it may be employed, for example, in the automated optical inspection of electrical circuits such as printed circuit boards. System 110 may, however, also be employed in the automated optical inspection of any suitable electrical circuit or other suitable article of manufacture, including flat panel displays, ball grid array substrates, multi-chip modules, integrated circuits and the like. Reference herein to printed circuit boards shall be deemed to include any other suitable article to be inspected.

As seen in FIGS. 2A–2E, an illuminator 118 is provided to illuminate portion 114, and a movable optical element 120, such as a pivotable planar mirror, a multi-faceted rotating polygon, a transparent rotating window, a transparent rotating polygon, or any other suitable passive or active optical element operative to affect a lateral translation of an image, is disposed in the optical path between sensor 112 and portion 114 of article 116 that is viewed by sensor 112. Illuminator 118 may be, for example, a light emitting diode, xenon flash, pulsed laser (such as Q-switched laser), a halogen or metal halide light source in combination with a suitable shutter, or any other suitable light source, providing generally wide spectrum illumination (such as "white" light), or light within a desired spectral range or monochrome light (such as colored light). The illumination may be visible or non-visible light such as UV or IR radiation. In accordance with an embodiment of the invention, illuminator is configured to produce illumination generally confined to portion 114 in order to minimize stray light.

A displacer (not shown) is provided to supply mutual translation between sensor 112 and article 116 along an axis generally lying in the direction of arrow 122. The displacer may be arranged to displace either object 116 or an optical assembly (not shown) including sensor 112, or both.

As seen in FIGS. 2A–2C and FIG. 2E, the portion 114 of object 116 viewed by sensor 112 extends for a finite length of the surface of article 116 at least partly along an axis lying in the direction of arrow 122. It is appreciated however that FIGS. 2A–2E are side view diagrams of system 110, and that sensor 112 preferably is formed of a two dimensional array of pixel elements 113, for example as depicted by sensor 13 in FIG. 1, such that its field of view extends, at least partly, both in the direction of arrow 22 and crosswise thereto along the surface of object 116.

In accordance with an embodiment of the invention, sensor 112 communicates with an image processor 124 via an I/O 126. Image processor 124 receives images of object 116 and performs various image processing steps operative to analyze the images and to provide an output, such as by defect detector 32 in FIG. 1, indicating the presence of defects in article 116. In the context of electrical circuit inspection, image processor 124 receives images of an electrical circuit pattern formed on the surface of article 116, and provides a report indicating the presence (or absence) of defects in the electrical circuit pattern.

Figure 2A:
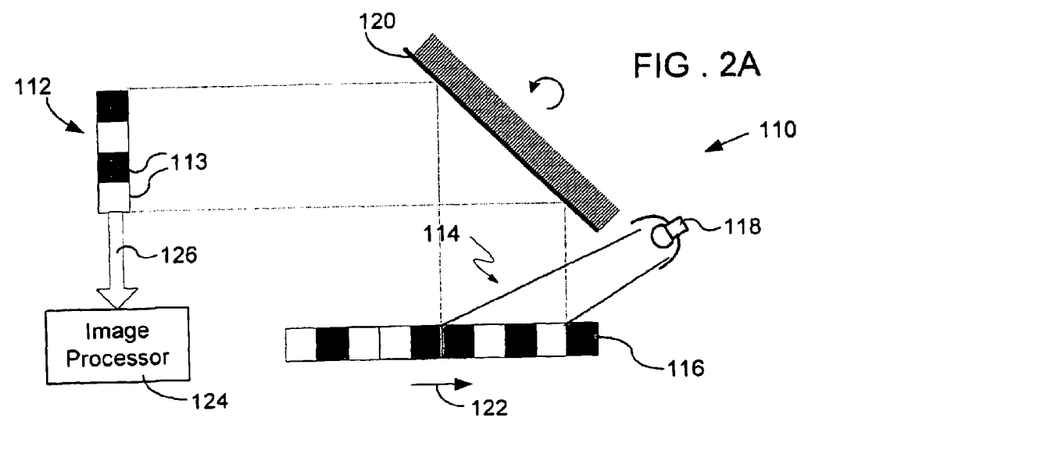
FIGS. 2A–2E are simplified schematic diagrams illustrating the operation of a system for the automated optical inspection of electrical circuits in accordance with an embodiment of the invention.
Figure 2B:
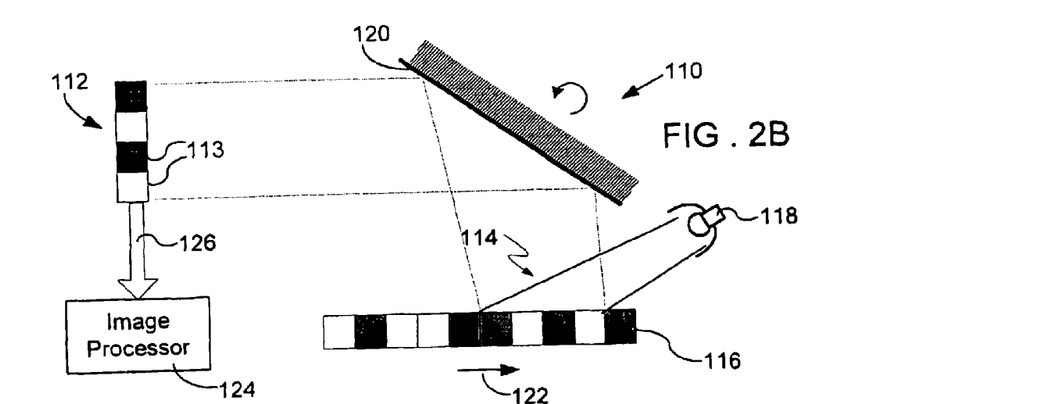
Figure 2C:
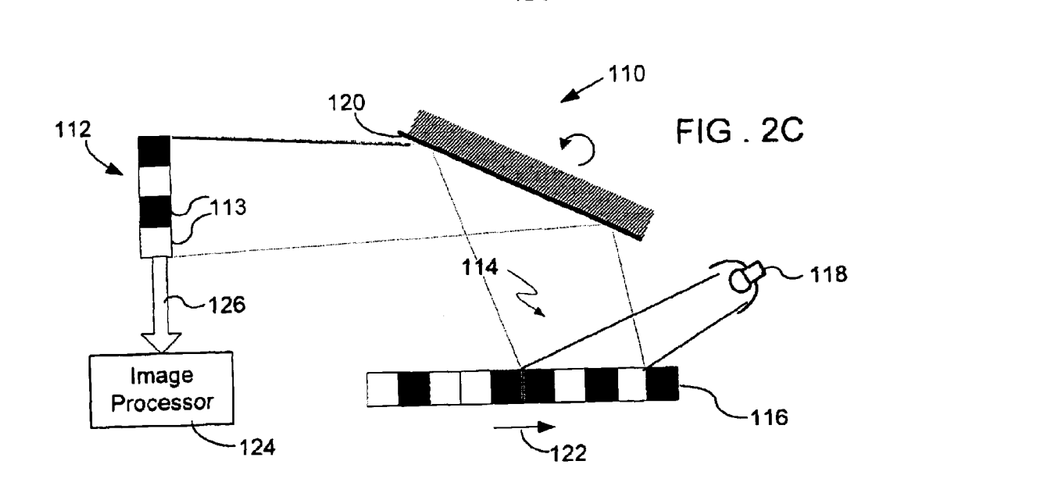

Sequential stages in the operation of system 110 are illustrated in FIGS. 2A–2C. In FIGS. 2A–2C it is seen that the spatial orientation of optical element 120, relative to sensor 112 and article 116, changes as article 116 progresses in the direction of arrow 122. This change in spatial orientation causes portion 114, viewed by sensor 112, to progress along with article 116, as article 116 and sensor 112 are mutually translated relative to each other. In accordance with an embodiment of the invention, the changing of spatial orientation of element 120 combines pivotal (or rotational) and linear motions in order to ensure that the image of portion 114 is maintained in focus at sensor 112 as the spatial orientation of element 120 is modified. A suitable structure for suitably modifying the spatial orientation of element 120 is described in U.S. Pat. No. 5,909,302, the disclosure of which is incorporated herein by reference in its entirety.

It is thus appreciated that by translating the field of view of sensor 12, covering portion 14, in synchroflicity with the relative translation between article 116 and sensor 112, charge can accumulate on pixels 113 for a relatively extended period of time, as compared to a conventional scanner, prior to reading off of the accumulated charge. In FIGS. 2A–2C, the accumulation of charge on sensor 112 is depicted by a progressive darkening of pixels 113, corresponding to locations in portion 114. In accordance with an embodiment of the invention, while charge is being accumulating on the pixels 113 of sensor 112, the charge is not read off, as depicted by the absence of fill in with respect to I/O 126.

It is noted that by translating the field of view of sensor 112 in synchronicity with the mutual translation of article 116 and sensor 112, the smearing of an image of portion 114 formed on sensor 112 is greatly reduced. It is noted that by reducing smear resulting from the mutual translation of article 116 and sensor 112, the exposure time of sensor 112 may be equal to several line periods. In other words, by translating the field of view of sensor 112, the time which an image is able to accumulate on sensor 112 is increased to several times the period that it would take a location, corresponding in size to a pixel 113, on article 116 to pass by a line of pixels 113 on sensor 112, but for the motion of optical element 120.

It is further noted that the increased exposure time resulting from freezing the field of view of sensor 112 in synchronicity with portion 114 enables the use of a lower intensity of illumination compared to a scanner employing a strobe without freezing the field of view of sensor 112. This is because charge can be accumulated for a relatively long period of time without smear. It is noted however that a high intensity strobe light may be employed to freeze an image without an opto-mechanical device to freeze the field of view. However in such an arrangement, the pulse width of such a strobe needs to be extremely short compared to the time between pulses, in order to minimize smear, while still providing a sufficient quantity of illumination.

In accordance with an embodiment of the invention, a strobing light source is used in order to generally freeze an image on sensor 112 to minimize image smearing. The duty cycle of the strobing light source preferably is in the range between 1:5 and 1:1000. In an embodiment of the invention, the strobing light source is employed in combination with means to synchronize between successive fields of view viewed by sensor 112 and successive portions 114.

Optionally, a strobing light is used without opto-mechanical means for freezing successive fields of view of sensor 112. However, as noted above, in such an arrangement, illumination having a relatively short pulse width in combination with relatively long time between pulses, for example a duty cycle exceeding 1:1000, is required. Such a high intensity strobe may be provided, for example, by a laser, such as a Q-switched laser or by modulated LEDs.

Figure 2D:
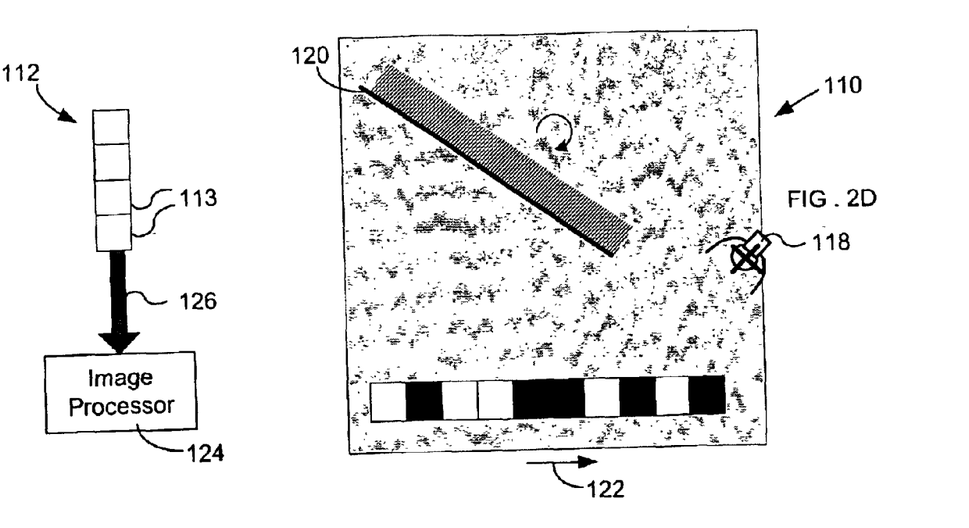

Referring now to FIG. 2D, it is noted that element 120 has a limited travel path within which it is able to maintain an image of portion 114 on sensor 112. Limits on the travel of element 120 typically result in portion 114 being less than the entirety of the surface of article 116. Once element 120 reaches the end of its travel path, its spatial orientation relative to sensor 112 must be reset to an initial spatial orientation relative to sensor 112, such that a successive portion of article 116 can be imaged. During the period in which the spatial orientation element 120 is reset, illuminator 118 preferably is turned off. Thus; in accordance with an embodiment of the invention, the modulation of illuminator 118, as the spatial orientation of element 120 is periodically reset, results in a strobe effect.

In accordance with an embodiment of the invention illuminator 18 is, for example, a LED source, which is strobed on and off in coordination with the reset period of optical element 20. It is noted that the turning of LED sources on and off enables the LEDs to cool down during the period that they are not turned on. It is further noted that the light output of LED sources is a function of a driving electric current, and that the usable driving current is limited by heat generated inside the LED. The inventors have found that strobing the LEDs, in accordance with an embodiment of the invention, increases their light output efficiency, as compared to continuous operation of the LEDs.

In accordance with an embodiment of the invention, LED illumination sources are operated at a higher level of current, and thus at a higher peak light output, in a strobed mode than possible when operated in a continuous light output mode. For "on" periods ranging between 100% and 10% of the cycle time, the inventors have found that the average light output varies little relative to a full continuous operation.

In accordance with an embodiment of the invention, during the period in which the charge on various pixels 113 of sensor 112 is read off, indicated in FIG. 2D by I/O 126 being filled in, illuminator 118 preferably is turned off and the orientation of element 120 is reset. It is noted that the configuration and structure of sensor 112 may vary, and that various different configurations of sensors, for example CCD sensors, CMOS type sensors and the like, may be used. A TDI type sensor may also be employed in system 110, provided that the orientation of element 120 is held stationary. In a TDI mode of operation, a continuous light source is used.

Figure 2E:
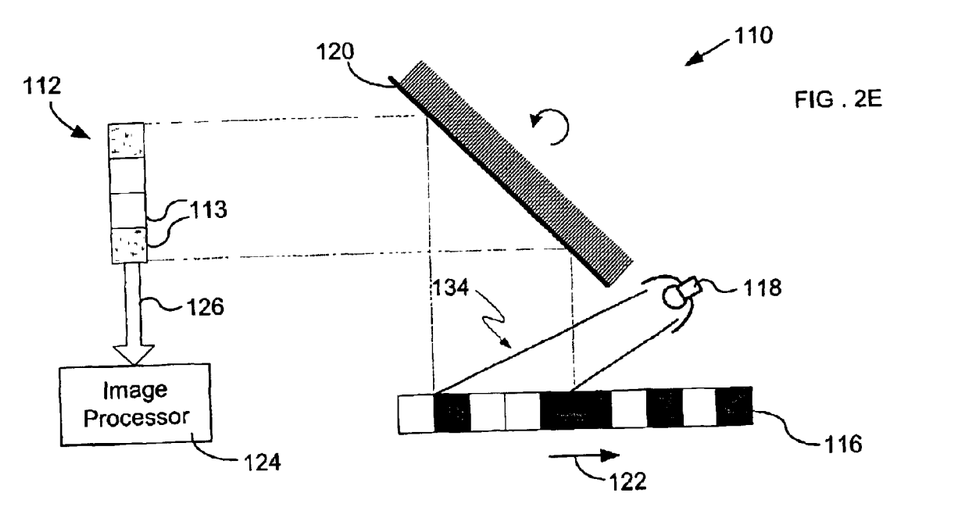

Referring now to FIG. 2E, it is seen that the spatial orientation of element 120 has been reset to the spatial orientation initially seen in FIG. 2A. However article 116 has progressed, relative to its orientation in FIG. 2A such that a successive portion 134 of the surface of article 116 is illuminated by illuminator 118 and viewed by sensor 112.

The sequence shown in FIGS. 2A–2E is repeated for successive portions 134 of article 116, each repeat commencing with the initial spatial orientation shown in FIGS. 2A and 2E respectively, until an image of the entire surface of article 116 is acquired. It will be appreciated that the rate of displacement of the article is generally uniform, and that the scanning of the field of view in synchronicity with the article (so as to keep the view temporarily fixed on the same portion of the article) and then resetting the field of view provides a rate of displacement of the field of view that is generally non uniform.

The field of view may cover substantially the entire width of the article, in which case movement in only one direction may be sufficient to provide coverage of the entire surface of interest. When the field of view covers less than the entire width of the article, the displacer should then be operative to provide displacement in two directions so that multiple passes, for example in a serpentine type travel path, can be made.

It is further noted, that a system employing the operational principles described hereinabove may be designed to selectively provide different alternative modes of operation, for example any one or more of the following examples of possible modes of operation: (1) a mode of operation in which element 120 is held stationary, illumination is continuous and the sensor is operated in a TDI mode; (2) a mode of operation in which element 120 is held stationary, very high intensity illumination is strobed, and the sensor is operated as a two dimensional staring array sensor imaging successive portions of an article; (3) a mode of operation in which element 120 is moved so as to freeze a field of a two dimensional staring array sensor on the article during image acquisition; and (4) a mode of operation in which element 120 is moved so as to freeze a field of a two dimensional staring array sensor on the article during image acquisition, and illumination is strobed in synchronicity with element 120.

Figure 3:
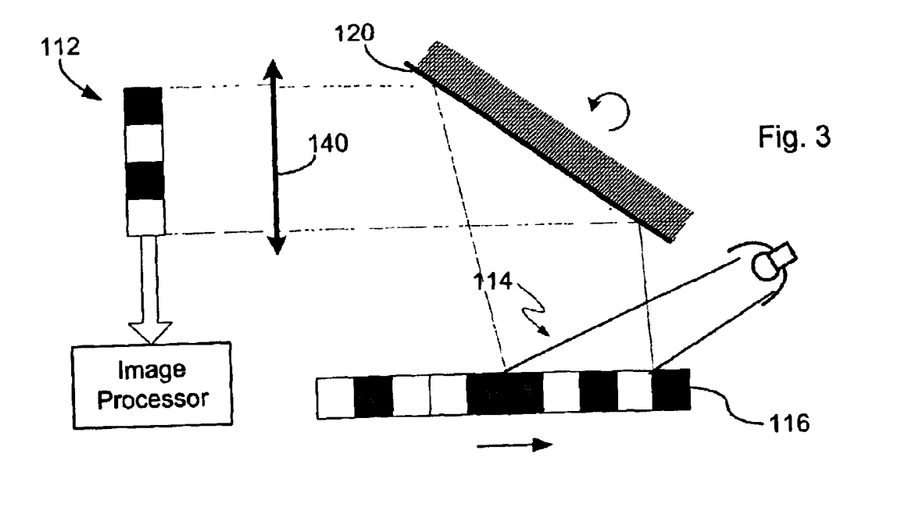
FIG. 3 is a simplified schematic diagram illustrating a first optical arrangement that may be employed in the system of FIGS. 2A–2E.
Figure 4:
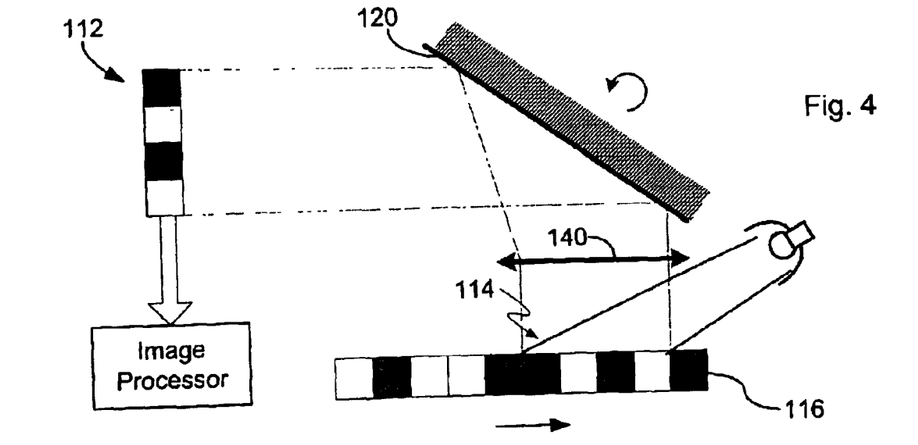
FIG. 4 is a simplified schematic diagram illustrating another optical arrangement that may be employed in the system of FIGS. 2A–2E.

Reference is now made to FIG. 3 and to FIG. 4 which are highly simplified schematic diagrams illustrating alternative preferred optical arrangements that may be employed in the system of FIGS. 2A–2E. Thus, in accordance with an embodiment of the invention, suitable imaging optics 140 forms an image of an illuminated portion 114 of article 116 on sensor 112. As seen in FIG. 3, imaging optics 140 may be located in the optical path extending between the surface of article 116 and sensor 112, downstream of the optical element 120 in relation to article 116. Alternatively, as seen in FIG. 4, imaging optics 140 may be located in the optical path extending between the surface of article 116 and sensor 112 upstream of the optical element 120 in relation to article 116.

Figure 5A:
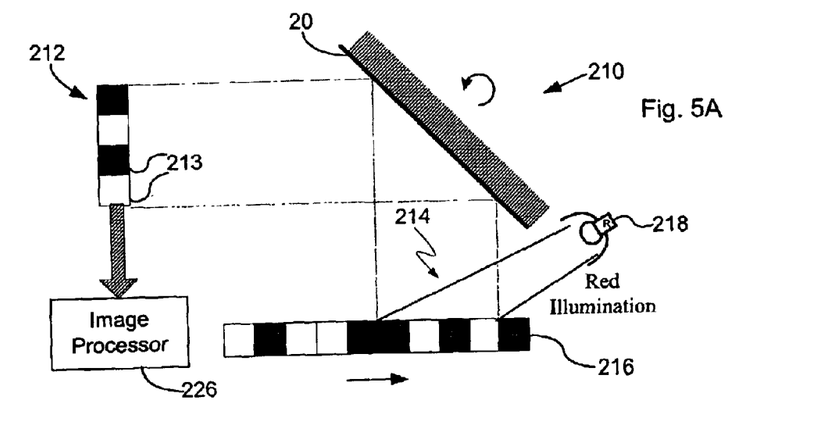
FIGS. 5A–5C are simplified schematic diagrams illustrating operation of the system of FIG. 2 in accordance with an alternative mode of operation.
Figure 5B:
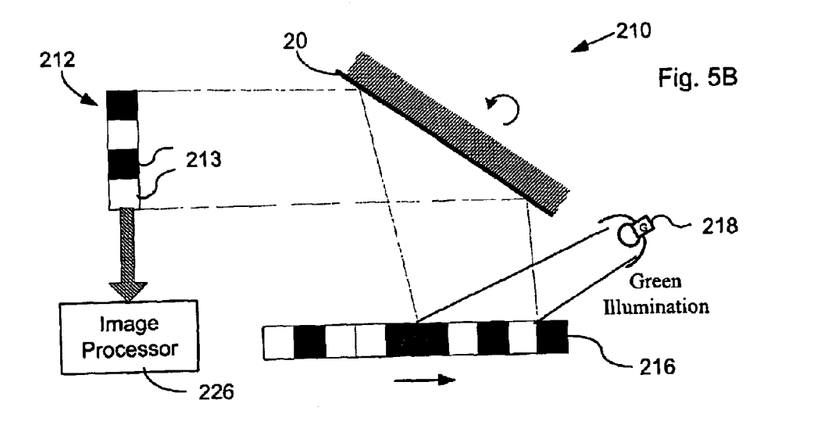
Figure 5C:
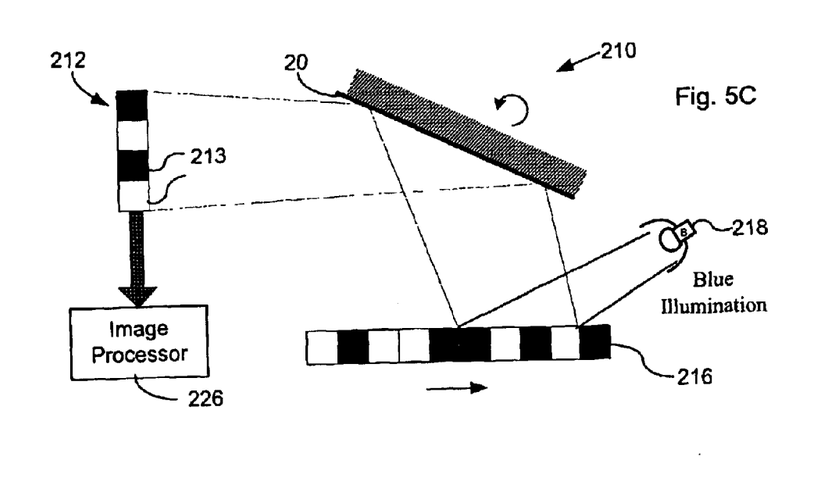

Reference is now made to FIGS. 5A–5C which are highly simplified schematic diagrams illustrating the operation of a system 210, similar in operation to system 110 seen in FIGS. 2A–2E, in accordance with another embodiment of the invention. In system 210 a plurality of images of the same portion 214 of surface of article 216 are sequentially acquired by sensor 212. That is to say, the illuminator is operative to illuminate the article using at least two different configurations of illumination, in a predetermined sequence. The different configurations of illumination may be, for example, illumination provided in different spectra (such as red illumination, green illumination and blue illumination), different configurations of non-polarized and differently polarized light, or different angles of illumination.

In accordance with an embodiment of the invention, the plurality of images of the same portion 214 of the surface of article 216 are respectively illuminated with red, green and blue illumination to provide, for example, Red, Green and Blue components, respectively, of a color image.

In accordance with an embodiment of the invention, system 210 relies upon the element 20 to freeze the field of view of sensor 212 in relation to portion 214 in order to provide a sufficient period of time for sensor 212 to acquire at least two substantially coincidental images. In the configuration of an embodiment of the invention, as seen in FIGS. 5A–5C, color imagery is provided by changing the spectrum of illumination for selected coincidental images of portion 214 of article or object 216.

In a first stage of operation of system 210, seen in FIG. 5A, a region 214 of object 216 is illuminated by an illuminator 218 with a first configuration of illumination, for example, illumination with red light. Charge is accumulated on pixels 213 of sensor 212 for the red illumination, read off, and provided to an image processor 226 for image processing and, subsequently, for defect detection.

In a second stage of operation of system 210, seen in FIG. 5B, the same region 214 of object 216 is illuminated by an illuminator 218 with a second configuration of illumination, for example, illumination with green light. Charge is accumulated on pixels 213 of sensor 212 for the green illumination, read off, and provided to an image processor 226 for image processing and, subsequently, for defect detection.

In a third stage of operation of system 200, seen in FIG. 5C, the same region 214 of object 216 is illuminated by an illuminator 218 with a third configuration of illumination, for example, illumination with blue light. Charge is accumulated on pixels 213 of sensor 212 for the blue illumination, read off, and provided to an image processor 226 for image processing and for subsequent defect detection.

In accordance with an embodiment of the invention, images acquired in each of the sequential stages are combined together to form a composite image, for example a color image, of the same portion of the article. Alternatively, the images that are acquired in each of the sequential stages, for example images that are acquired, respectively, with brightfield and with darkfield illumination, are considered separately, for example in separate image inspection operations.

In accordance with an embodiment of the invention, illuminator 218 comprises separate light sources. Each of the separate light sources may constitute a separate illuminator. Alternatively, the light sources may be combined so as to form a single illumination unit. In accordance with an embodiment of the invention, the light sources are, for example, arrays of red, green, and blue light emitting diodes, respectively.

A light homogenizer, not shown, may be provided to ensure uniform illumination by each of the red, green and blue light sources, even when the light sources are spatially offset one from the other. In accordance with an embodiment of the invention, colored LED light sources are employed such that light loss associated with conventional spectral filters is obviated. The color balance of color images generated from temporally separated coincidental images which are each illuminated by a different spectrum of illumination may be adjusted by balancing the respective intensity of each of the sources of illumination, or alternatively, by tuning the respective spectrum emitted by one or more of the light sources.

In accordance with an embodiment of the invention, Red, Green and Blue LED arrays, each emitting their particular spectrum, are strobed in an interleaved manner in order to form corresponding coincidental images. As previously noted, the strobing of color LEDs further improves illumination efficiency of the LED light sources. Optionally, it is appreciated that illuminator 218 may be a broad spectrum emitter provided with suitable spectral filters.

Following the acquisition of corresponding images of portion 214, the spatial orientation of element 220 is reset, as described hereinabove with respect to FIG. 2D, and the sequence of acquiring multiple substantially coincidental images is repeated for sequential portions of the surface of object 216. The multiple substantially coincidental images for all of the various portions 214 on article 216 are combined. In accordance with an embodiment of the invention, combination of the coincidental images, each acquired using a staring array scanner as described hereinabove, in combination with illumination in suitable spectra, generates a high resolution color image files defined by corresponding red, green and blue pixels which are not mutually spatially offset. Such color image files are particularly useful for color image processing and defect detection in, for example, the field of automated optical inspection of electrical circuits.

In accordance with an embodiment of the invention, system 210 thus provides for the acquisition of a sequence of corresponding images of the same portion 214 of the surface of an article 216 all by the same sensor, despite the mutual relative translation of sensor 212 and object 216. Each of the corresponding images may be combined together in image processor 226 to provide, for example, a color or other desired multi-component image of object 216. Such a color image is desirable in that, despite continuous relative translation between a sensor and an object, each of the spectral components of the color image is acquired with the same monochrome sensor array, resulting in color image files defined by spectral image components whose corresponding pixels are all in precise mutual alignment.

It is appreciated by persons skilled in the art that the present invention is not limited by what has been particularly shown and described hereinabove. Rather, the present invention includes modifications and variations thereof which would occur to a person of skill in the art upon reading the foregoing description and which are not in the prior art.

What is claimed is:

1. An inspection system for inspecting articles for defects, comprising:
    a sensor comprising a two dimensional array of pixels and being operative to acquire an image of each of at least two different portions of an article, said sensor and said article being continuously mutually displaced relative to each other;
    an image freezer rotating synchronously with the mutual relative displacement between said sensor and said article, thereby forming a motionless image of a portion of said article on said sensor while said sensor acquires said image, during said mutual relative displacement; and
    a defect detector operative to analyze said images to detect defects in said article.

2. The inspection system claimed in claim 1 and wherein said portions are each two dimensional portions of said article.

3. The inspection system claimed in claim 1 and wherein the width of said portions covers at least the entire width of said article.

4. The inspection system claimed in claim 1 and wherein the width of said portions covers less than the entire width of said article.

5. The inspection system claimed in claim 4 and wherein said mutual relative displacement is provided in a first direction, and then in a second direction.

6. The inspection system claimed in claim 1 and wherein said image freezer is operative during said mutual relative displacement to align a field of view of said sensor with a first portion of said article for a given period of time and then to align said field of view with a second portion of said article for said given period of time.

7. The inspection system claimed in claim 1 and wherein said image freezer comprises a movable optical element interposed between said article and said sensor.

8. The inspection system claimed in claim 7 and wherein said image freezer is operative during said mutual relative displacement to align a field of view of said sensor with a first portion of said article for a given period of time and then align said field of view with a second portion of said article for said given period of time.

9. The inspection system claimed in claim 8 and wherein said movable optical element is moved from a first spatial orientation to a second spatial orientation during said given period of time.

10. The inspection system claimed in claim 9 and wherein said movable optical element is reset to said first spatial orientation to align said field of view with said second portion of said article.

11. The inspection system claimed in claim 10 and further comprising an illuminator illuminating said article.

12. The inspection system claimed in claim 11 and wherein said illuminator is modulated such that said illuminator illuminates said article while a field of view of said sensor is aligned to said first portion, and said illuminator does not illuminated said article during the reset of said movable optical element.

13. The inspection system claimed in claim 1 and wherein said image freezer comprises a modulated illuminator that is modulated to non-continuously illuminate said article.

14. The inspection system claimed in claim 13 and wherein said modulated illuminator has a duty cycle which is sufficient to freeze images acquired by said sensor during said mutual relative displacement.

15. The inspection system claimed in claim 14 and wherein said duty cycle is in excess of about 1:1000.

16. The inspection system claimed in claim 15 and wherein said modulated illuminator comprises LEDs.

17. The inspection system claimed in claim 15 and wherein said modulated illuminator comprises a xenon flash.

18. The inspection system claimed in claim 14 and wherein said modulated illuminator comprises a pulsed laser.

19. The inspection system claimed in claim 18 and wherein said pulsed laser is a Q-switched laser.

20. An inspection system for inspecting articles for defects, comprising:
    a sensor acquiring an image of at least one portion of an article during relative mutual displacement between said sensor and said portion, said sensor defining a field of view;
    a field of view translator operative to scan said field of view across said article synchronously with said relative mutual displacement, and periodically reset said field of view; and
    a defect detector operative to analyze said image of at least one portion to detect defects in said article.

21. The inspection system claimed in claim 20 and wherein said sensor comprises a two dimensional array of pixels.

22. The inspection system claimed in claim 20 and wherein said field of view covers at least the entire width of said article.

23. The inspection system claimed in claim 20 and wherein said field of view covers less than the entire width of said article.

24. The inspection system claimed in claim 23 and wherein said mutual relative displacement is provided in a first direction, and then in a second direction.

25. The inspection system claimed in claim 20 and wherein said field of view translator is operative during said mutual relative displacement to align said field of view with a first portion of said article for a given period of time and then to align said field of view with a second portion of said article for said given period of time.

26. The inspection system claimed in claim 20 and wherein said field of view translator comprises a movable optical element interposed between said article and said sensor.

27. The inspection system claimed in claim 26 and wherein said field of view translator is operative to align said field of view with a first portion of said article for a given period of time and then align said field of view with a second portion of said article for said given period of time.

28. The inspection system claimed in claim 27 and wherein said movable optical element is moved from a first spatial orientation to a second spatial orientation during said given period of time.

29. The inspection system claimed in claim 28 and wherein said movable optical element is reset to said first spatial orientation to align said field of view with said second portion of said article.

30. The inspection system claimed in claim 29 and further comprising an illuminator illuminating said article.

31. The inspection system claimed in claim 30 and wherein said illuminator is modulated such that said illuminator illuminates said article while said field of view is aligned to said first portion, and said illuminator does not illuminate said article during the reset of said movable optical element.

32. The inspection system claimed in claim 20 and further comprising a modulated illuminator that is modulated to non-continuously illuminate said article in synchronicity with said non-uniform rate of scanning.

33. The inspection system claimed in claim 32 and wherein said illuminator is operative to illuminate said article with at least two different spectral configurations of illumination, according to a predetermined sequence.

34. An inspection system for inspecting defects in articles, comprising:
a sensor comprising a two dimensional array of pixels and defining a field of view, said filed of view viewing an article during mutual relative displacement thereof relative to said sensor;
a field of view translator operative to translate said field of view during said mutual relative displacement, synchronously with said mutual relative displacement, such that a motionless image of a first portion of said article is formed on said sensor for a period of time that is at least as long as an image acquisition time required by said sensor to acquire an image of said first portion; and
a defect detector operative analyze images acquired by said sensor to detect defects in said article.

35. The inspection system claimed in claim 34 and wherein said field of view translator comprises a movable optical element interposed between said article and said sensor.

36. The inspection system claimed in claim 35 and wherein said field of view translator is operative to move said optical element from a first spatial orientation relative to said sensor to a second spatial orientation relative to said sensor during said period of time to freeze an image of a first portion of said article on said sensor.

37. The inspection system claimed in claim 36 and wherein said field of view translator is operative to reset said optical element to said first spatial orientation following said period of time, such that an image of a second portion is formed on said sensor.

38. The inspection system claimed in claim 37 and wherein said second portion is adjacent to said first portion.

39. The inspection system claimed in claim 37 and wherein said second portion partially overlaps said first portion.

40. The inspection system claimed in claim 35 and wherein said movable optical element is a planar mirror configured to be pivoted during said relative mutual displacement between said article and said sensor to freeze the location of an image of a portion of said article on said sensor.

41. The inspection system claimed in claim 40 and wherein said planar mirror is configured to be linearly translated while being pivoted.

42. The inspection system claimed in claim 35 and wherein said movable optical element is a rotating polygon.

43. The inspection system claimed in claim 34 and wherein said field of view translator comprises a sensor displacer operative to displace said sensor such that said field of view is displaced synchronously with said mutual displacement.

44. The inspection system claimed in claim 34 and further comprising: an illuminator periodically illuminating said article while said sensor is acquiring an image of said portion, wherein said illuminator has a duty cycle of greater than 1:100.

45. The inspection system claimed in claim 44 and wherein said illuminator has a duty cycle of greater than 1:10.

46. The inspection system claimed in claim 45 wherein said illuminator has a duty cycle of greater than 1:5.

47. The inspection system claimed in claim 44 and wherein said illuminator is synchronized with said sensor and with said field of view translator such that while said illuminator is illuminating said article said field of view translator is operative to translate said field of view and said sensor is operative to acquire said image, and while said illuminator is not illuminating said article said field of view translator is operative to reset said field of view to view a second portion of said article and said sensor is operative to output an acquired image of said first portion.

48. The inspection system claimed in claim 34 and wherein said article is an electrical circuit.

* * * * *